United States Patent [19]
Ringel et al.

[11] Patent Number: 5,285,687
[45] Date of Patent: Feb. 15, 1994

[54] PROCESS FOR THE ACOUSTIC EXAMINATION OF MONOLITHS FOR DAMAGE AND DEVICE FOR IMPLEMENTING THE PROCESS

[75] Inventors: Werner Ringel, Neusass; Peter Kugland, Friedberg; Enrique Santiago, Diedorf, all of Fed. Rep. of Germany

[73] Assignee: Zeuna-Starker GmbH & Co. KG, Augsburg, Fed. Rep. of Germany

[21] Appl. No.: 761,359
[22] PCT Filed: Dec. 7, 1990
[86] PCT No.: PCT/EP90/02115
§ 371 Date: Oct. 7, 1991
§ 102(e) Date: Oct. 7, 1991
[87] PCT Pub. No.: WO91/10131
PCT Pub. Date: Jul. 11, 1991

[30] Foreign Application Priority Data
Dec. 28, 1989 [DE] Fed. Rep. of Germany ....... 3943133

[51] Int. Cl.⁵ .............................................. G01H 3/08
[52] U.S. Cl. .................... 73/579; 73/12.01; 73/12.14
[58] Field of Search ............. 73/12, 579, 584, 12.01, 73/12.04, 12.14

[56] References Cited
U.S. PATENT DOCUMENTS

| | | | |
|---|---|---|---|
| 2,388,246 | 11/1945 | Berger | 73/12 |
| 3,097,523 | 7/1963 | Diamond et al. | 73/584 |
| 4,342,229 | 8/1982 | Massa | 73/579 |
| 4,858,469 | 8/1989 | Hosgood et al. | 73/579 |
| 5,144,838 | 9/1992 | Tsubol | 73/579 |

FOREIGN PATENT DOCUMENTS

| | | |
|---|---|---|
| 56772 | 7/1982 | European Pat. Off. |
| 2531440 | 3/1976 | Fed. Rep. of Germany |
| 58-147642 | 9/1983 | Japan ................ 73/584 |

Primary Examiner—John E. Chapman
Attorney, Agent, or Firm—Helfgott & Karas

[57] ABSTRACT

A method and apparatus for the acoustic examination of a monolith for damage, wherein a blow of defined force is applied by a hard striker to a monolith for its acoustic examination for damage. The sound pressure distribution over a predetermined frequency range, of the sound radiated by the struck monolith is analyzed by a frequency analyzer and the result is compared with a reference curve defined for undamaged monoliths. The device for implementing the process has a receptacle for the monolith to be examined, a striker, capacitor microphones as the sound pressure receivers and an evaluation unit with a frequency analyzer.

23 Claims, 3 Drawing Sheets

PROCESS FOR THE ACOUSTIC EXAMINATION OF MONOLITHS FOR DAMAGE AND DEVICE FOR IMPLEMENTING THE PROCESS

BACKGROUND OF THE INVENTION

The present invention relates to a process for the acoustic examination of monoliths for damage as well as a device for carrying out the process.

Monolithic carrier elements, as are used, for example, during the manufacture of waste gas catalysts and soot filters for motor vehicles, consist usually of relatively porous ceramic materials. The considerable porosity of the material used leads to possible damage of the monoliths during their manufacture or further processing; in particular, during handling of a monolith, fine cracks can form at the latter's surface or its interior. Such cracks render the carrier element practically unusable, since they constitute a starting point for a possible break of the monolith at a later time; a destruction of such cracked monoliths may take place already during relatively small loads, for example, due to jarring during their processing and/or during operation. For this reason, monolithic carrier elements must not be processed further, even if they have been damaged only slightly.

Therefore, it is required to examine carrier elements for possible damage prior to further processing. In addition to an optical examination, which naturally can address merely the condition of the surface, an acoustic examination takes place as well. For this purpose, a trained person lightly taps the monolith and evaluates the noise subsequently emitted by the monolith. For this purpose, the understanding is taken into consideration that cracks in the interior of the monolith influence the latter's vibration behavior and thus the radiated frequencies.

With such an acoustic examination, various disadvantages are connected: For one thing, the reproduceability is not satisfactory, because the subjective sound perception by the person conducting the test is critical to the result of the examination. Also, the striking location and strength, carried out manually in the known process for acoustic examination, influence the result of the examination inasmuch as the resulting variation in loudness of the radiated sound alters the sound perception of the examining person. Thus, all in all, a low degree of reliability results from the conventional acoustic examination, which in practice is expressed by a large portion of monoliths which can neither be clearly classified as flawless nor clearly as damaged. After, for safety reasons, only those monoliths are processed further, which have been classified as clearly flawless, the shown unreliability of the testing method used leads to a relatively high rejection rate during the production and thus to higher manufacturing costs.

SUMMARY OF THE INVENTION

Accordingly, it is an object of the present invention to create a process for the acoustic examination of monoliths for damage, which distinguishes itself by a high degree of reliability.

According to the invention, this object is attained by means of a process comprising the following procedural steps:

To a fixed monolith, a blow of defined magnitude is administered by means of a hard striker;
the sound pressure distribution over a frequency range, radiated by the monolith is analyzed by means of a frequency analyzer in the form of an evaluation unit;
the result of the analysis is compared with a reference curve defined for undamaged monoliths.

Through the use of a frequency analyzer for determining pressure/frequency distribution of the radiated noise, the uncertainties resulting from the known testing process through subjective hearing perception of the test personnel are reliably excluded. The comparison of the analysis result with a reference curve applicable to undamaged monoliths also contributes to the increase in the reliability of the testing process. In this connection, it is also of great importance to realize that undamaged and damaged monoliths, particularly with respect to their sound pressure distribution at high frequencies (for example, between 4 and 12 kHz), are distinguishable, while human hearing has its greatest degree of sensitivity near approximately 1 kHz. The fact that the sensitivity of human hearing within the frequency spectrum, which is of considerable significance for distinguishing between damaged and undamaged monoliths, is considerably less than in the case of lower frequencies, may be seen as an explanation for the relatively high error rate during the conventional testing procedure. With the process of the invention, the basically insufficient suitability of human hearing no longer plays a role for the purpose at hand.

In a preferred arrangement of the process of the invention, synchronously at least two sound pressure measurements are carried out in varying directions of diffusion. After the sound pressure diffusion, radiated in a certain direction (in space) has been influenced to a considerable degree by the position and alignment of the crack inside the monolith, it cannot be excluded in the case of a single sound pressure measurement in only one direction of diffusion that a "disadvantageously" located crack remains undetected. While carrying out two or more synchronous sound pressure measurements in varying directions of diffusion, however, a displacement of the sound pressure diffusion will always occur which is such that the crack is identified. Thus, the step of carrying out synchronously at least two sound pressure measurements in varying diffusion directions contributes to a further increase in the reliability of the process of the invention. In the case of a cylindrical monolith, it is particularly preferable to carry out precisely two sound pressure measurements of which one takes place in axial direction and the other one in radial direction. This is applicable in the same way for circular cylindrical monoliths, as well as for those cylindrical monoliths with another base surface, such as an ellipse.

As already presented, a characteristic displacement of the sound pressure distribution takes place in the case of damaged monoliths particularly in the range between 4 and 12 kHz, for which reason in the case of a preferred arrangement of the process of the invention, the frequency analysis is preferably limited to this range. Most preferably, the comparison of the analysis result with the reference curve does not take place in the entire spectrum but only in individual selected reference points.

For this purpose, the reference points for the individual monolith type are characteristic frequencies, i.e., in particular such frequencies in which the sound radiated by the struck monolith has a particularly high sound pressure. In the case of these frequencies, the reference curve has so-called "peaks." Here the reference points are here determined for the respective monolith type in a series of pre-tests.

The comparison of the analysis result with the reference curve takes place preferably in a computer unit which is connected with the evaluation unit. Thus, the comparison can take place in particular through the comparison of the peaks with respect to their frequency, their number in a predetermined frequency band and/or with respect to their amplitude (sound pressure).

In a preferred arrangement of the process of the invention, during the sound pressure analysis, the impact sound of the striker is not taken into consideration. In this way, a falsification of the measurement of the radiated frequencies is prevented by the noise occurring during impact of the striker with the monolith; rather, the sound pressure analysis is limited exclusively to the radiated noise and for this reason has a greater signal strength with respect to the state of the tested monolith. Particularly preferably, the sound pressure analysis sets in between 5 and 30 ms after impact of the striker.

Preferably, the striker is part of a pendulum and is released during each testing process from the same point along the pendulum path. In this way it is achieved that the impact force applied to the monolith always has the same, easily determinable magnitude. The striker impacts in the case of cylindrical monoliths preferably with one of the front faces, particularly in their center.

One arrangement which is suitable for carrying out the process of the invention has a recess for accommodating the monolith to be tested, a striker arrangement comprising a movable striker, at least one sound pressure receiver and an evaluation unit connected with the sound pressure receiver (the sound pressure receivers).

For this purpose, the evaluation unit comprises preferably a computer unit, carrying out the comparison of the analysis result produced in the evaluation unit with the reference curve. Preferably, an indicator unit is connected with the computer unit which indicates the result of the examination.

In order to permit the placement of various types of monoliths in the receptacle, the latter comprises preferably three supports for the placement of the monolith. Alternatively thereto, the construction of the receptacle is in the form of a holding plate, which has at least one holding element adjusted to the respective monolith type. Here the supports or the holding element have preferably damping elements made of an elastically resilient material in order to ensure a vibration decoupling. The striker arrangement has preferably a pendulum carrier as well as a pendulum on which the striker is provided. Such a pendulum assures a particularly high uniformity in the impact force transferred from the striker to the monolith which in turn is of great significance for the reproduceability of the measuring results. It is particularly advantageous if, for this purpose, the striker consists of a ferromagnetic material and the striker arrangement comprises an electromagnet arranged in the upper final point of the pendulum path of the striker. With an arrangement constructed in this way, the testing process is initiated in that the electromagnet is rendered current-free, whereby the ferromagnetic striker is released and, following the predetermined pendulum path, impacts with the monolith.

The evaluation unit of the device of the invention is preferably such that it controls the start of the frequency analysis depending on the impact of the striker with the monolith. At that time, the control assigned to the evaluation unit releases the frequency analysis preferably between 5 and 30 ms after that point in time at which the striker impacts with the monolith; the information regarding the time of impact and the impact noise is directed to the evaluation unit by one or several sound pressure receivers. In order to determine the sound pressure/frequency distribution, the evaluation unit preferably has an FFT-analyzer, i.e., the sound pressure distribution is determined by means of a "Fast Fourier Transform" [process]. Capacity microphones are particularly preferred as sound pressure receivers.

DETAILED DESCRIPTION OF THE PREFERRED EMBODIMENTS

Figure 1:
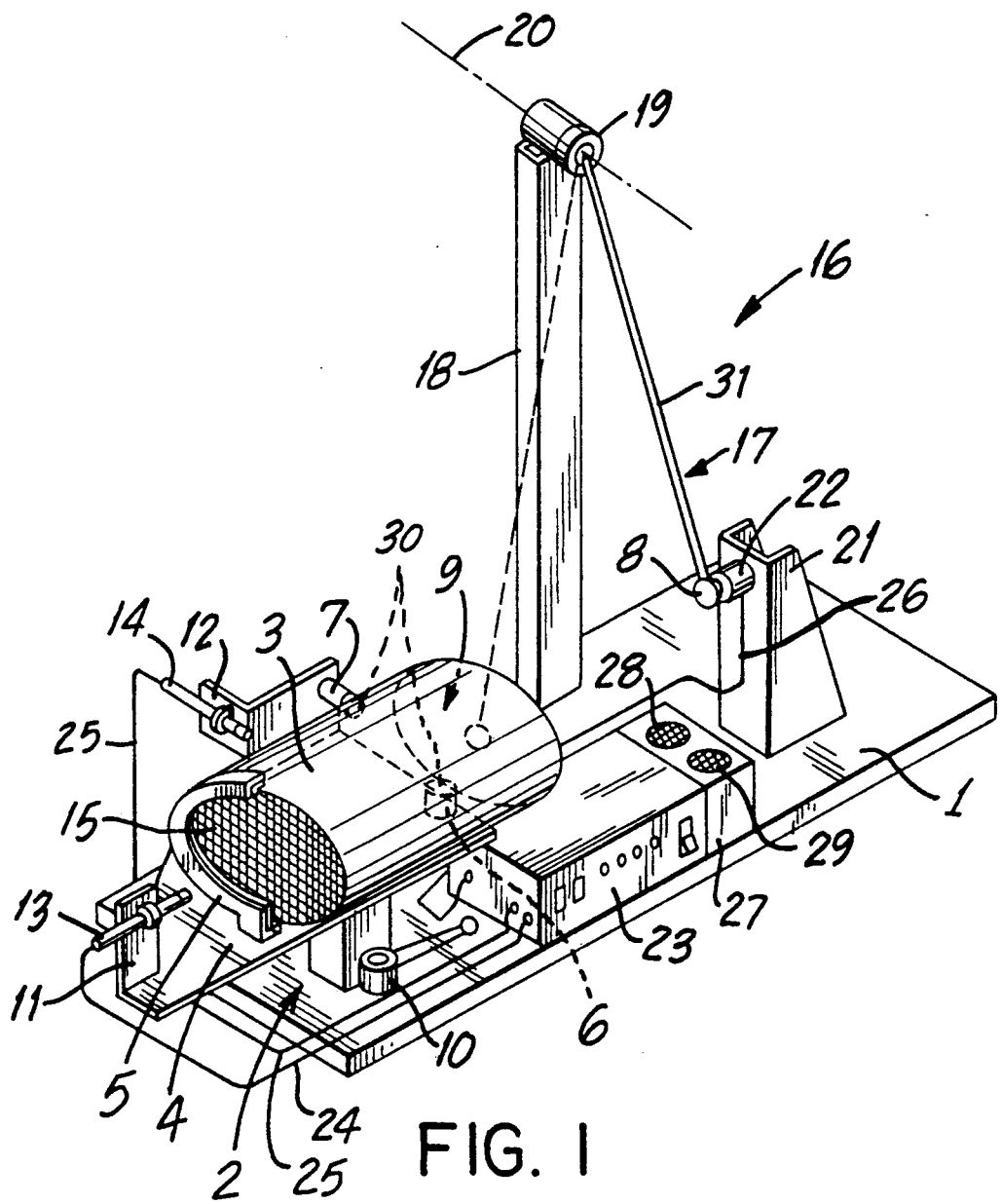
FIG. 1 shows an embodiment of a device for carrying out the process of the invention.

The testing device according to FIG. 1 is constructed on a baseplate (1). On the baseplate (1), a receiving element (2) for a monolith (3) is erected. The receiving element (2) comprises a holding plate (4), carrying a front holding element (5) as well as a lower stop (6) and a lateral stop (7) for the monolith (3). While the front holding element (5) fixes the monolith (3) particularly in its axial direction, the two stops (6, 7) serve to adjust the monolith in such a way, that a striker (8) impacts precisely in the center of the rear face, i.e., the face (9) of the monolith (3) which is at a distance from the holding element (5). The stops (6, 7), as well as the holding element (5), have at their contact surfaces with the monolith (3) damping elements (30) made of elastically resilient material.

The holding plate (4) is attached to the baseplate (1) by means of a quick-gripping device (10), whereby two receiving elements (2) which are adjusted to various monolith types, can be rapidly exchanged with each other. At the holding plate (4), two microphone holders (11, 12) are provided, each of which has a capacitor microphone (13, 14). For this purpose, a capacitor microphone (13) faces the front face (15) of the monolith (3), while the other capacitor microphone (14) is directed towards the peripheral surface of the monolith (3).

The striker device (16) comprises a pendulum (17), its free end carrying the striker (8) in the form of a steel ball. The pendulum (17) is suspended from a boom (18), which is rigidly connected with the baseplate (1). The pendulum (17) has a pendulum rod (31) in the form of a stiff pipe which reaches the boom (18) by means of a ball bearing (19), pivotable about a horizontal axis (20).

Furthermore, on the baseplate (1), a magnet carrier (21) is located, at the front face of which, facing the monolith (3), an electromagnet (22) is attached. Also, the baseplate (1) comprises an evaluation unit (23) with an integrated computer unit, i.e., the measuring, evaluation and comparison electronics are accommodated inside the same housing. The capacitor microphones (13, 14) are connected via lines (24, 25) with the evaluation unit (23). The electromagnet (22) is connected with the evaluation unit (23) via a line (26). An indicator unit (27), coupled with the computer unit, has two indicator lamps (28, 29); the indicator lamp (28) lights up when the tested monolith has been found by the computer unit (23) to be defective; in comparison, the indicator lamp (29) lights up when a repetition of the test is required, for example, as a result of a faulty operation of the testing device.

Figure 2A:
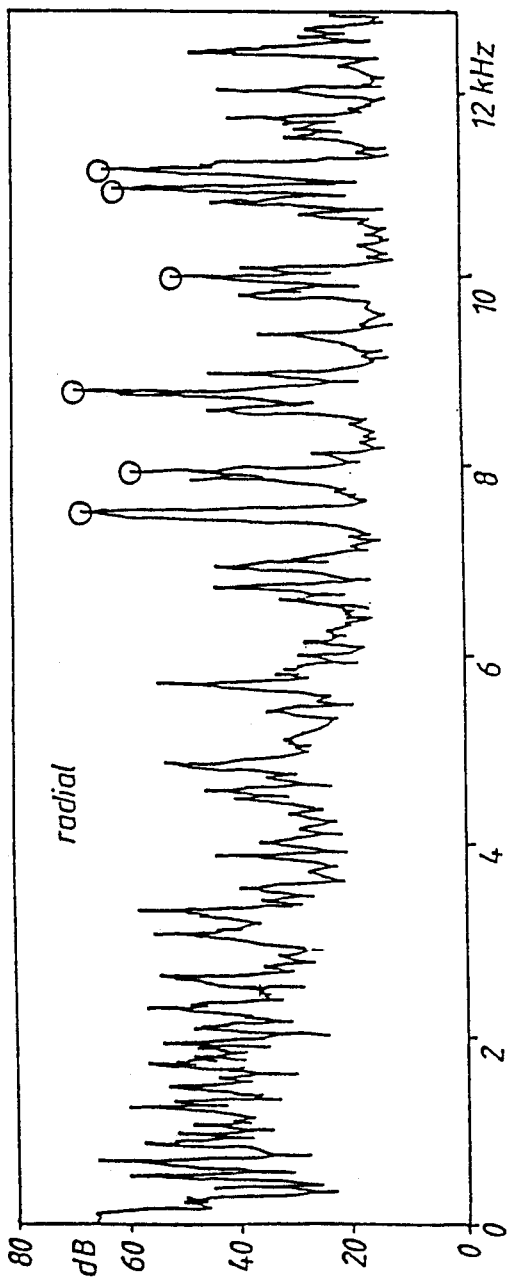
FIGS. 2A and 2B show a sound pressure distribution in an undamaged monolith.
Figure 2B:
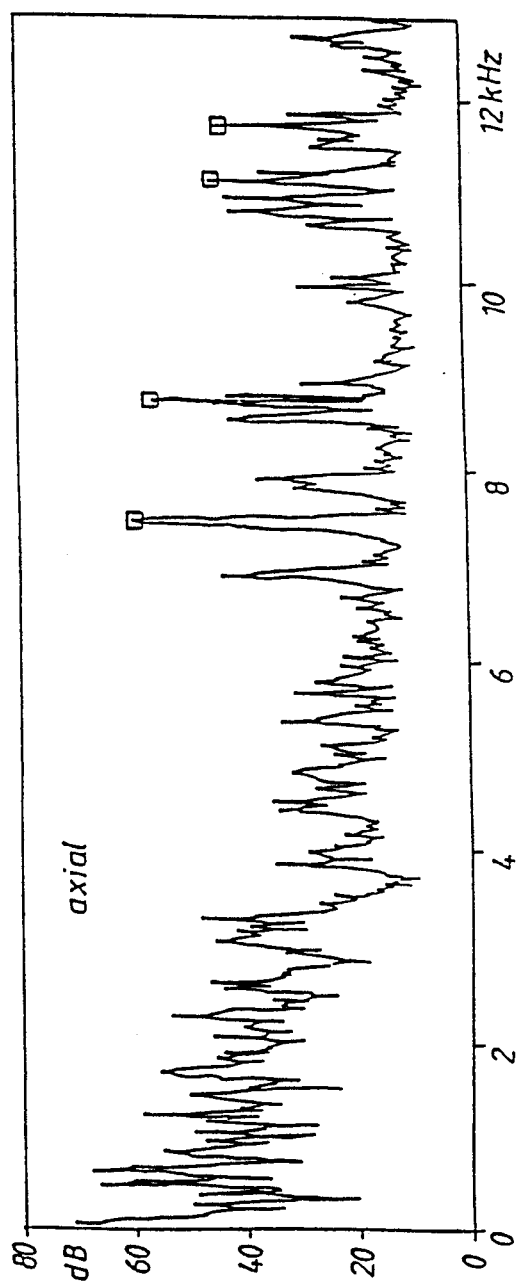

FIGS. 2A, 2B sow a sound pressure distribution over a frequency range as shown as it was determined for an undamaged elliptical-cylindrical monolith (3), measuring 6.68"×3.18"×6" (16.97 cm ×8.08 cm ×15.24 cm). The considered frequency spectrum extends from 0 to 12.8 kHz and is recorded on the abscissa. The scaling for the sound pressure provided on the ordinates axis spans from 0 to 80 dB.

The distribution demonstrated in FIG. 2A was determined by means of the microphone (14) (FIG. 1), arranged laterally with respect to the monolith (3); the sound pressure/frequency distribution shown in FIG. 2B was determined by means of the microphone (13) (FIG. 1) directed against the front face (15). For the test demonstrated in FIGS. 2A, 2B the computer unit was set to a 10 ms post trigger, i.e. during the frequency analysis, the first 10, ms continued to be disregarded when the striker (8) impacted with the monolith (3).

Figure 3A:
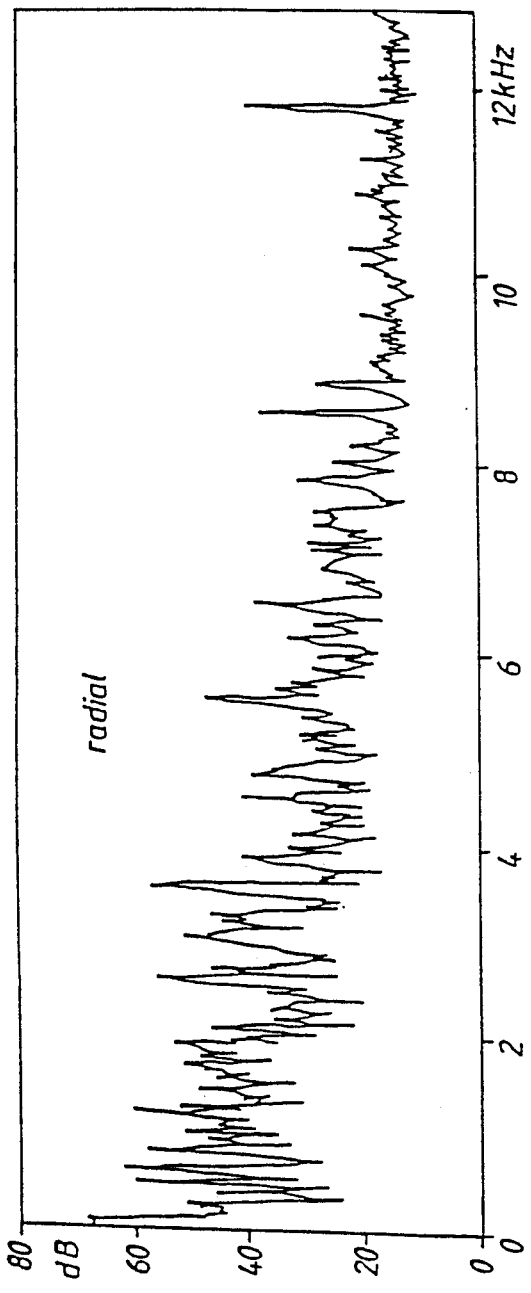
FIGS. 3A and 3B show a sound pressure distribution in damaged monolith, wherein in the FIGS. 2A, 2B and 3A, 3B two measuring curves are shown each, determined in varying directions of distribution.
Figure 3B:
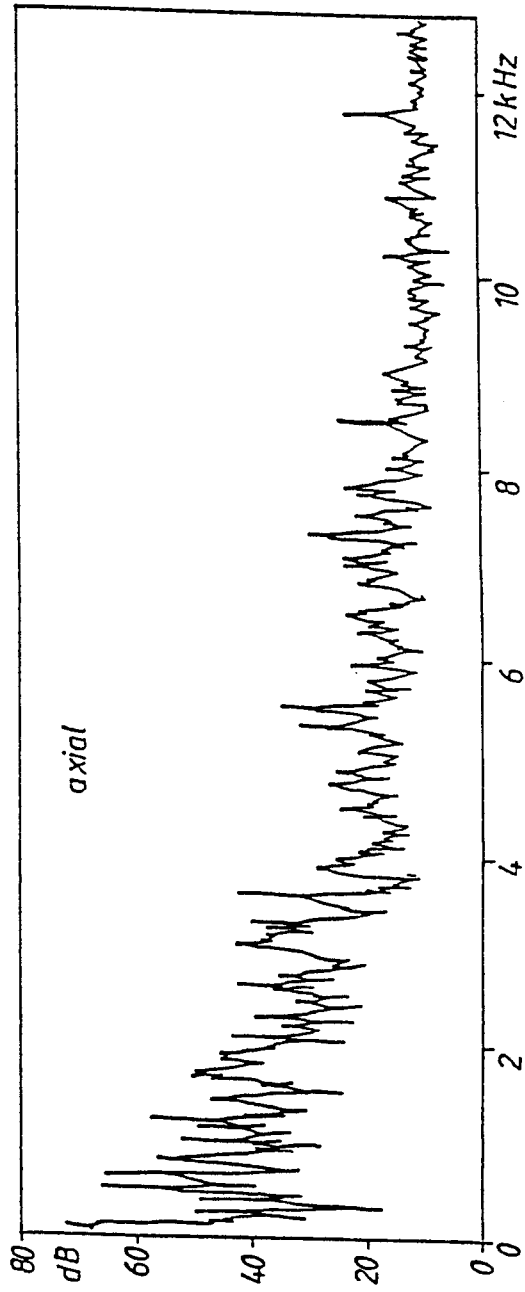

FIGS. 3A, 3B show a sound pressure distribution over a frequency range shown for a defective monolith of the same type determined under the same test conditions. FIGS. 3A, 3B clearly show that in the case of a defective monolith, particularly in the frequency range above 6 kHz, the distinctive sound level peak values of FIGS. 2A, 2B, characterizing the undamaged monolith, do not occur. Particularly conspicuous through their absence are the peak values present with the undamaged monolith, and lying at 7.4; 7.9; 8.7; 10.0; 10.9 and 11.1 kHz of the sound pressure distribution, determined by means of the laterally arranged microphone (FIG. 2A, circle marks). Thus, the named frequencies form characteristic reference frequencies for the type of monolith tested. The same is applicable to the frequencies 7.4, 8.7, 10.8, 11.2 and 11.7 kHz with respect to the frontally arranged microphone (FIG. 2B, box like marks).

We claim:

1. A process for the acoustic examination for damage of monolithic carrier elements of porous ceramic material for use in manufacturing of waste gas catalysts, the process comprising the steps of:

fixing a monolithic body of porous ceramic material to be examined, to a stationary plate;

applying an impact force of a predetermined magnitude to a fixed monolithic body by means of a hard striker;

performing synchronously at least two measurements of sound pressure of the noise radiated by the struck body, determining from said measurements, with a time delay after the striker has struck the fixed body, sound pressure distribution over a predetermined frequency range by means of a frequency analyzer in an evaluation unit to obtain an analysis result in which an impact noise of the striker is not taken into consideration due to said time delay; and comparing selected individual values of sound pressure obtained in said analysis result with reference values of sound pressure defined in a sound pressure reference curve for undamaged monolithic bodies, wherein said at least two sound pressure measurements are performed in varying spreading directions, and wherein said monolithic body is a cylindrical body, and one of the two sound pressure measurements is carried out in an axial direction of said cylindrical body and the other one in a radial direction of said cylindrical body.

2. Process in accordance with claim 1, wherein said time delay is in the range of 5 to 30 ms.

3. Process in accordance with claim 1, wherein the sound pressure distribution within the frequency range between 4 and 12 kHz is determined in said determining step.

4. Process in accordance with claim 1, wherein said said selected individual values are compared with reference values in said comparing step at frequencies of characteristic peaks of said curve.

5. Process in accordance with claim 1, wherein a number of peaks within said predetermined frequency range of a curve obtained in said analysis result are compared with a number of peaks in said reference curve in said comparing step.

6. Process in accordance with claim 1, wherein said striker is formed as a pendulum and each examination procedure starts from the same point of a pendulum path.

7. Process in accordance with claim 1, wherein the striker impacts one of end faces of said cylindrical body.

8. Process in accordance with claim 7, wherein the striker impacts in the center of a front face of the monolithic body.

9. Process in accordance with claim 1, wherein said comparing step is carried out in a computer unit.

10. Process in accordance with claim 9, and further comprising the step of providing an indicator unit connected with said computer unit wherein said computer unit controls said indicator unit so that said indicator unit indicates whether the noise radiated by the monolithic body being examined lies within or outside the reference curve.

11. A device for the acoustic examination for damage of monolithic carrier elements of porous ceramic material for use in manufacturing of waste gas catalysts, the device comprising:

receptacle means for holding a a cylindrical monolithic body of porous ceramic material, being examined;

a striker assembly including a movable striker for applying an impact force of a predetermined magnitude to said monolithic body fixed in said receptacle means;

sound pressure receiver means for performing synchronously at least two sound pressure measurements in varying spreading directions, of the noise radiated by a struck monolithic body; and an evaluation unit including a computer unit and connected to said sound pressure receiver means for determining from said measurements, with a time delay after the striker has struck the fixed monolithic body, sound pressure distribution over a predetermined frequency range to obtain an analysis result in which an impact noise of the striker is not taken into consideration due to said time delay and comparing selected individual values of sound pressure obtained in said analysis result with reference values of sound pressure defined in a sound pressure reference curve for undamaged monolithic bodies.

12. Device in accordance with claim 11, and further comprising an indicator unit connected to said computer unit for indicating whether the monolithic body being examined has been found by said evaluation unit to be defective.

13. Device in accordance with claim 11, wherein said receptacle means includes three supports for placement of the monolithic body being examined.

14. Device in accordance with claim 11, wherein said receptacle means includes a holding plate and at least one support in the form of a holding element adapted to a monolithic to be examined.

15. Device in accordance with claim 14, wherein said holding plate is attached on a baseplate by a quick-gripping device.

16. Device in accordance with claim 13, wherein each of said supports has at each of points of contact with the monolithic body to be examined, damping elements made of an elastically resilient material.

17. Device in accordance with claim 11, wherein said striker assembly further comprises a pendulum having a pendulum rod on which the striker forms a pendulum mass.

18. Device in accordance with claim 17, wherein said striker consists of a ferromagnetic material and the striker assembly further comprises an electromagnet arranged at an upper end point of a pendulum path of the striker.

19. Device in accordance with claim 11, wherein said sound pressure receiver means includes two sound pressure receivers which are arranged in such a way that one receiver is directed towards a front end face facing away from the striker assembly and the other receiver is directed towards a peripheral surface of the monolithic body to be examined.

20. Device in accordance with claim 19, wherein said two sound pressure receivers are capacity microphones.

21. Device in accordance with claim 11, wherein said evaluation unit comprises an FFT-frequency analyzer.

22. Device in accordance with claim 11, wherein said computer unit is constructed to provide said time delay in the range between 5 and 30 ms after the striker has struck the monolithic body.

23. Device in accordance with claim 12, wherein said indicator unit includes lamps.

* * * * *